(12) United States Patent
Watanabe (10) Patent No.: US 8,788,282 B2
(45) Date of Patent: Jul. 22, 2014

(54) VIRTUAL HEALTH CARE NEEDS FULFILLMENT SYSTEM

(75) Inventor: Gregory G Watanabe, Poway, CA (US)

(73) Assignee: Medimpact Healthcare Systems, Inc., San Diego, CA (US)

( * ) Notice: Subject to any disclaimer, the term of this patent is extended or adjusted under 35 U.S.C. 154(b) by 214 days.

(21) Appl. No.: 12/203,785

(22) Filed: Sep. 3, 2008

(65) Prior Publication Data

US 2010/0057489 A1 Mar. 4, 2010

(51) Int. Cl.
*G06Q 10/00* (2012.01)
*G06Q 40/00* (2012.01)
*G06Q 50/00* (2012.01)
*A61B 5/00* (2006.01)

(52) U.S. Cl.
USPC ............................................. 705/2; 600/300

(58) Field of Classification Search
USPC .......................................................... 705/2
See application file for complete search history.

(56) References Cited

U.S. PATENT DOCUMENTS

| | | | |
|---|---|---|---|
| 5,301,105 A | 4/1994 | Cummings, Jr. |
| 5,704,044 A | 12/1997 | Tarter et al. |
| 5,737,539 A | 4/1998 | Edelson et al. |
| 5,845,255 A | 12/1998 | Mayaud |
| 6,108,635 A | 8/2000 | Herren et al. |
| 6,195,612 B1 | 2/2001 | Pack-Harris |
| 6,283,761 B1 | 9/2001 | Joao |
| 7,165,077 B2 | 1/2007 | Kalies |
| 7,490,047 B2 | 2/2009 | Brown et al. |
| 7,505,917 B2 | 3/2009 | Howe et al. |
| 7,949,580 B1 | 5/2011 | Boyer et al. |
| 8,060,379 B1 | 11/2011 | Pinsonneault et al. |
| 8,069,059 B2 | 11/2011 | Howe et al. |
| 8,099,295 B2 | 1/2012 | Virdee et al. |
| 8,265,950 B2 | 9/2012 | Howe et al. |
| 8,346,571 B2 * | 1/2013 | Kalies, Jr. ........................ 705/2 |
| 2001/0037216 A1 | 11/2001 | Oscar et al. |
| 2002/0002495 A1 | 1/2002 | Ullman |
| 2002/0049617 A1 | 4/2002 | Lencki et al. |
| 2002/0095316 A1 | 7/2002 | Toan et al. |
| 2002/0111832 A1 | 8/2002 | Judge |
| 2002/0120473 A1 | 8/2002 | Wiggins |
| 2002/0147617 A1 | 10/2002 | Schoenbaum et al. |
| 2002/0169727 A1 | 11/2002 | Melnick et al. |
| 2002/0183965 A1 | 12/2002 | Gogolak |

(Continued)

FOREIGN PATENT DOCUMENTS

| | | |
|---|---|---|
| WO | WO 95/24010 | 9/1995 |
| WO | WO 97/44752 | 11/1997 |

OTHER PUBLICATIONS

"Cost Sharing Strategies for OHP Medical Services." pp. 1-5. Revised Jul. 5, 2001.

(Continued)

*Primary Examiner* — Hiep V Nguyen
(74) *Attorney, Agent, or Firm* — Foley & Lardner LLP (57) ABSTRACT

A method of operating a health care needs fulfillment system, by: (a) a PBM contracting with a plurality of health care suppliers to fulfill a plurality of health care needs requests; (b) end users sending individual health care needs requests to the PBM; (c) the PBM selecting the health care suppliers to supply each of the end users' individual health care needs requests; and (d) the PBM alerting the selected health care suppliers to fulfill the end users' individual health care needs requests.

19 Claims, 3 Drawing Sheets

(56) References Cited

U.S. PATENT DOCUMENTS

| | | |
|---|---|---|
| 2003/0154106 A1 | 8/2003 | Marks |
| 2004/0054685 A1 | 3/2004 | Rahn et al. |
| 2004/0073457 A1 | 4/2004 | Kalies |
| 2004/0133452 A1 | 7/2004 | Denny et al. |
| 2004/0143171 A1 | 7/2004 | Kalies |
| 2004/0143594 A1 | 7/2004 | Kalies |
| 2004/0148195 A1 | 7/2004 | Kalies |
| 2004/0148196 A1 | 7/2004 | Kalies |
| 2004/0148198 A1 | 7/2004 | Kalies |
| 2004/0148498 A1 | 7/2004 | Kailes |
| 2004/0230502 A1 | 11/2004 | Fiacco et al. |
| 2005/0060188 A1 | 3/2005 | Valley |
| 2005/0065821 A1 | 3/2005 | Kalies, Jr. |
| 2005/0071193 A1 | 3/2005 | Kalies |
| 2005/0071200 A1 | 3/2005 | Franklin et al. |
| 2005/0240442 A1 | 10/2005 | Lapsker |
| 2005/0261939 A1 | 11/2005 | Augspurger et al. |
| 2005/0283259 A1 | 12/2005 | Wolpow |
| 2006/0020514 A1 | 1/2006 | Yered |
| 2006/0116905 A1* | 6/2006 | Yered ............................... 705/2 |
| 2006/0129357 A1 | 6/2006 | Francis et al. |
| 2006/0178915 A1 | 8/2006 | Chao |
| 2006/0184391 A1* | 8/2006 | Barre et al. ....................... 705/2 |
| 2006/0271402 A1 | 11/2006 | Rowe et al. |
| 2007/0011025 A1 | 1/2007 | Cracchiolo et al. |
| 2007/0050210 A1 | 3/2007 | Wiley, II |
| 2007/0106623 A1 | 5/2007 | Melnick et al. |
| 2007/0250341 A1* | 10/2007 | Howe et al. ....................... 705/2 |
| 2008/0312956 A1 | 12/2008 | Momita et al. |
| 2009/0076868 A1 | 3/2009 | Malone et al. |
| 2009/0144082 A1 | 6/2009 | Selbst et al. |
| 2009/0177488 A1 | 7/2009 | Unland et al. |
| 2009/0177490 A1 | 7/2009 | Howe et al. |
| 2009/0281823 A1 | 11/2009 | Hardaway |
| 2009/0281824 A1 | 11/2009 | Hardaway |
| 2009/0319311 A1 | 12/2009 | Mi et al. |
| 2009/0326975 A1 | 12/2009 | Hardaway et al. |
| 2010/0161351 A1 | 6/2010 | Howe et al. |
| 2010/0217622 A1 | 8/2010 | Brown et al. |
| 2010/0287002 A1 | 11/2010 | Barre et al. |
| 2010/0312578 A1 | 12/2010 | Hardaway |
| 2011/0029321 A1 | 2/2011 | Rourke et al. |
| 2011/0054935 A1 | 3/2011 | Hardaway |

OTHER PUBLICATIONS

Laing, R.O., et al., "Tuberculosis Drug Issues: Prices, Fixed Dose Combination Products and Second Line Drugs", Journal Tuberculosis Disease, 4(12) S194-S207 (Feb. 2000).

Huskamp, H.A., et al., "The Medicare Prescription Drug Benefit: How Will the Game be Played?" Health Affairs, 19(2) 8-23 (Mar.-Apr. 2000).

Lipton, H.L., et al., "Managing the Pharmacy Benefit in Medicare HMOs: What Do We Really Know?" Health Affairs, 19(2) 42-58 (Mar.-Apr. 2000).

MedImpact Medicare Part D 2009 Pre-Processing Drug List (PPDL) White Paper, Updated Mar. 25, 2008. pp. 1-5.

MedImpact Medicare Part D 2008 Pre-Processing Drug List (PPDL) White Paper, Updated Mar. 25, 2008. pp. 1-5.

MedImpact Medicare Part D Pre-Processing Drug List (PPDL) White Paper, Updated Jul. 20, 2006. pp. 1-5.

MedImpact Medicare Part D Drug List White Paper, Oct. 13, 2005. pp. 1-4.

Infocrossing Healthcare Services, Inc., Prescription Drug Event (PDE) Submission Process Summary, 2007, Infocrossing, pp. 1-2.

Comments of Generic Pharmaceutical Association for the Public Meeting on Proposed Changes to the National Drug Code System; RIN 0910-AA49; Nov. 24, 2006; 7 pages.

PCT International Search Report, mailed Jul. 8, 2007, in PCT/US06/42976.

Medicare Program: Revisions to the Medicare Advantage and Prescription Drug Benefit Programs; The Federal Register (FIND73.096); May 16, 2008; Source: Dept. of Health and Human Services.

* cited by examiner

VIRTUAL HEALTH CARE NEEDS FULFILLMENT SYSTEM

TECHNICAL FIELD

The present invention relates to systems for filling patients' medical prescriptions and to systems for supplying durable medical equipment to end users.

BACKGROUND OF THE INVENTION

Many employees and members ("consumers") of health maintenance organizations, employer groups and government entities have their purchases of personal prescription medications subsidized by payments to pharmacies through prescription benefit plans ("plans") offered by those health maintenance organizations, employer groups and government entities. Under such plans, a consumer receives a prescription for a medication from his or her physician and submits it to a pharmacy to be filled. The pharmacy checks to see that the consumer is a member of a plan with which the pharmacy has a contract and that the medication and dosage prescribed are within the approved scope of the plan contract. Upon verification of these requirements, the pharmacy dispenses the medication to the consumer. The consumer pays the pharmacy a "copay" amount, less than the normal cost of the medication. The pharmacy receives the balance of the payment for the medication and its dispensing services from the prescription benefit plan, which is managed by a "prescription benefit manager" ("PBM") with whom the health maintenance organization, employer group or government entity ("payer") has contracted to manage the plan. The PBM invoices the payer (i.e., the PBM's customer) for the consumer's transaction, along with a charge for its contracted fee, and from the funds paid by the payer the PBM pays the pharmacy's balance due.

Medication usage is commonly differentiated between acute care usage, which is short term (30 days or less) administration to treat immediate illnesses or conditions, and maintenance usage, which is long term (more than 30 days) treatment of chronic illnesses or conditions such as hypertension, high cholesterol levels, arthritis, neurology conditions and the like. Maintenance medication dispensing and usage represents a major health care cost (on the order of 75% of prescription costs for many plans, especially due to the aging of the American population) and therefore control of maintenance prescription costs is a principal function of the prescription benefit plans. Dispensing pharmacies are normally of two types: retail pharmacies (which are local neighborhood businesses where the consumer appears in person, can meet with a pharmacist, orders his/her medication and can usually leave a few minutes later with the dispensed medication in hand) and mail order pharmacies (which are large facilities, usually not open to individual consumers' personal visits, but from which a consumer's medication order received by mail or through the Internet is subsequently filled and dispensed to the consumer via mail or courier service). It is normally recognized by the industry that acute care prescriptions are dispensed primarily by retail pharmacies, since the consumer frequently needs the medication immediately and cannot accept the multi-day delay inherent in submitting and dispensing prescription medications from the mail order pharmacies.

On the other hand, PBMs and benefit consultants commonly strongly urge or even mandate that consumers in the plans that they administer obtain their maintenance medications from mail order pharmacies. It is a widely held belief that mail order pharmacies may have lower operating costs and may offer greater discounts available on medication coverage. To the extent that such is the case, use of mail order pharmacies may be a desirable cost control strategy if other contractual terms remain equalized. However, several factors can complicate the analysis of use of mail order pharmacies versus use of retail pharmacies especially for dispensing of maintenance medications. For instance, some PBMs own mail order pharmacies, and therefore it is to their financial benefit to steer the consumers in their plans to their captive pharmacies whether or not that is in the best interest of the consumers. Further, to the extent that business is diverted unreasonably from retail pharmacies to mail order pharmacies, the former are deprived of income. Since the retail pharmacies are commonly localized businesses (in contrast to mail order pharmacies), their ability to survive to provide the local retail service is impaired. This is true even when a local pharmacy is part of a larger chain pharmacy organization, since decline in income of a local site could lead the chain to close that local site, notwithstanding that other locations of the chain's pharmacies remain in business. Further, there are many variables in the pricing of medications and the costs involved in inventories, dispensing equipment, transportation of medications to the pharmacy and later to the consumer and staffing, that have been shown to affect whether mail order does or does not have a financial advantage over retail in the dispensing of medications. All that can be said is that, properly managed, both types can be financially and commercially viable.

Further, and very significantly, there is a question of availability of choice for the consumer, since in many cases a consumer would like to have the option of dealing either with his/her local pharmacy or a mail order pharmacy. Numerous studies have established that for many prescription consumers, direct contact with a pharmacist is very important. Professional pharmacists are held in very high regard by consumers and their advice is eagerly sought. Most consumers are not knowledgeable about medications and a prescribing physician's schedule may not provide sufficient time for a consumer to be able to get what he or she believes to be sufficient information from the prescribing physician about all aspects of concern about a prescribed medication. Consumers want to be able to speak directly to their pharmacists for more information about their medications and receive detailed answers to their questions and concerns, especially when a maintenance medication which will be taken by the consumer over a prolonged period is involved. It is well known that the prospects for a consumer's (patient's) successful implementation of a medication regimen are greatly enhanced when the consumer/patient understands and is comfortable with the medication prescribed. Such direct and personal contact with a pharmacist is frequently difficult for a consumer to obtain from a mail order pharmacy, and even when available will almost certainly not involve a pharmacist who is "local" to the consumer and his/her community.

Because the cost of medications is so high and is such a large component of medical care costs generally, there is an on-going effort on the part of PBMs and payers to seek ways in which to control medication costs. Pharmaceutical medications are commonly available to consumers (patients) either in "brand name" (proprietary) or generic form. In some cases, especially for new or patented medications, only the brand name medication is available, usually only from a single source—the developer of the medication. For many others, however, there is no proprietary limitation on manufacture of the medication, and multiple sources of the medication—in generic or alternative brand name form—are available. Further, it is common that for a given class of pharmaceuticals, there are several different medications with substantially equivalent medical and physiological effects. Some of these medications may be proprietary brand name products while others may be generic and yet others may have be available in both generic and brand name forms. Retail prices charged by pharmacies can vary widely, especially where a particular medication is available in both brand name and generic form. Reimbursement rates paid to pharmacies vary depending on the product based on traditional reimbursement methodologies.

Physicians and other health care providers who write prescriptions therefore often have choices among the different medications they can prescribed for a patient. A physician can, for instance, prescribe a brand name medication or a generic form of that medication, or he/she can choose between two or more different but equivalent medication compositions. If the physician prescribes a brand name medication, he/she can also designate whether a dispensing pharmacy must dispense only that specific medication or can substitute an equivalent generic medication. There are of course significant differences in retail cost among the different medication forms, with generic forms normally being substantially lower in cost than brand name medications. However, either within each group (brand name or generic) there can be substantial cost differences, depending usually on the wholesale prices set by the various manufacturers. Thus for a single therapeutic category a physician, pharmacy and patient may be faced with numerous forms of the same or equivalent medications, all with different pricing.

What would instead be desired is a system in which the pharmacy best suited to fulfill a prescription is the pharmacy that is actually selected to fulfill the prescription. Ideally, such a system would quickly match pharmacies to the prescription requests that they are best suited to fulfill. Preferably, this matching would be accomplished in a manner that reduces costs, but does not rely solely upon pricing/costs to determine which pharmacy is best suited to fulfill each prescription. Preferably as well, this system would simplify prescription ordering services and operate with minimum burden on the patients using the system to fulfill their prescriptions. In addition, this system would preferably select either mail order or retail pharmacies—depending upon which is best suited to fulfill each particular patients' prescriptions. Also, this system would preferably work with pharmacies/suppliers of both "brand name" and generic medications such that the cost differences between equivalent medications can be taken into account. For example, by selecting a pharmacy that supplies generic medication when a physician has written a "brand name" prescription.

For the reasons set forth above, many patients today are not able to optimally select the best pharmacy for their needs. Instead, they are simply attracted to on-line mail order pharmacies to reduce prescription costs. Although many patients are able to obtain prescription medications at reduced costs, the use by patients of on-line mail order pharmacies have some serious disadvantages, as follows.

First, the patient typically is only able to select the purported "best" mail order pharmacy on the basis of medication cost. As such, there is no ability for a patient to select the best pharmacy on any other basis, including but not limited to: pharmacy expertise, the pharmacy's physical location, and/or the appropriateness of any substitute or generic medication. As such, most patients are not properly qualified to make assessments of which pharmacy is "best" for their particular prescription fulfillment.

Second, the patient is typically only seeking to have one prescription filled at a time. It would instead be more efficient if patients could pool their prescription needs such that different pharmacies could specialize in fulfilling different prescriptions (thereby providing optimal costs and services). This would also permit different pharmacies to more efficiently manage their inventories.

Third, patients typically have to decide between dealing with an "in-person" pharmacy or an "on-line" pharmacy. It is difficult for a patient to simultaneously utilize or compare both in-person and on-line pharmacies. This is problematic since one particular in-person or on-line pharmacy may be best suited to fill one of the patient's prescriptions, while another particular in person or on-line pharmacy may be best suited to fill another of the patient's prescriptions. Moreover, the same patient may have different prescription requests—with a retail pharmacy being best suited to fulfill one prescription and a mail order pharmacy being best suited to fulfill another prescription.

Fourth, the need exists for a coordinated system to manage and track patient prescription fulfillment. The data from such a system could ideally be used to track prescription ordering histories and to provide data that can be analyzed to determine how to increase prescription fulfillment efficiencies.

SUMMARY OF THE INVENTION

In one aspect, the present invention provides a method of operating a health care needs fulfillment system, comprising: (a) a PBM contracting with a plurality of health care suppliers to fulfill a plurality of health care needs requests; (b) end users sending individual health care needs requests to the PBM; (c) the PBM selecting the health care suppliers to supply each of the end users' individual health care needs requests; and (d) the PBM alerting the selected health care suppliers to fulfill the end users' individual health care needs requests. After the PBM has alerted the selected health care suppliers, the selected health care suppliers then fulfill the end users' individual health care needs requests.

In one preferred aspect, the end users are patients, the health care needs requests are prescription requests, and the health care suppliers are pharmacies. In various aspects of the invention, any single selected pharmacy may be selected to supply the same prescriptions to different patients, to supply different prescriptions to the same patient, and/or different prescriptions to different patients. Moreover, different pharmacies may be selected to supply identical prescriptions to different patients (for example, when the selection of the pharmacy is based on the relative locations of the patients and the pharmacy). As such, different selected pharmacies may supply the same or different prescriptions to the same or different patients. Thus, any patient may receive one or more prescriptions from one or more of the selected pharmacies. It is to be appreciated that all combinations of prescription fulfillment are thereby contemplated within the scope of the present invention.

In various aspects, the prescriptions may be filled by mail-order, or in person. Different patient's prescriptions may be filled differently. For example, some may be filled by mail-order, and some in person (depending upon the pharmacy selected by the PBM. In various preferred aspects, the prescription is pre-approved prior to the PBM alerting the pharmacy to fill the prescription. This further increases the efficiency of the present invention.

One advantage of the present system is that the PBM selects the pharmacy best suited to fill each of the prescriptions submitted by the patients. This is preferred since the PBM has far more expertise (than the patients) in selecting pharmacies. Moreover, by having the PBM pre-contract with selected pharmacies for selected prescriptions, the PBM can negotiate and secure large supplies of particular routine medications. This would enable the PBM to secure a preferred cost for the medications that are supplied. This is also advantageous to the pharmacy that is selected since it would then have a guaranteed contract to supply a large number of identical medications. This would permit a selected pharmacy to better plan its inventories, and build up larger stores of particular medications as needed.

The present invention is thus preferable over traditional on-line pharmacy systems in which a patient simply invites pharmacies to bid for his/her prescription, and then selects the lowest cost pharmacy. In such traditional on line systems, the "bulk bidding" or "bulk supplying" of medications is not possible since only a single prescription is bid on (one at a time) by the various pharmacies. A further disadvantage of such traditional on line systems is that the pharmacies can only bid on supplying the prescription after the patient has send in the prescription request. It would instead be preferable for pharmacies to secure contracts to supply large volumes of prescriptions ahead of time (and plan their inventories accordingly).

In accordance with the present invention, the PBM selects the pharmacies, thereby matching individual prescription requests to pharmacies best suited to fill these requests. The PBM may select the best pharmacy to fill each prescription on the basis of quality of service and health outcomes (based on patient surveys), price, the location of the pharmacy and the patient, on the basis of particular pharmacy expertise (i.e., pharmacy that employs a pharmacist with diabetes certification or other clinical designations), or any other criteria relevant to the PBM. Also, the pharmacies are typically pre-selected by the PBM prior to the individual patient prescription requests being received by the PBM. For example, the PBM can look at historical data to forecast prescription demands. It is to be understood, however, that the present invention encompasses both methods where the pharmacies are pre-selected (prior to the patient sending in their prescription requests), and where the pharmacies are selected after the patient sends in their prescription requests. The latter case may occur when the patient has an unusual or rare prescription request that must be looked at by the PBM prior to the PBM selecting the best pharmacy to fill the prescription request.

In some optional aspects, the PBM contracting with a plurality of health care suppliers to fulfill a plurality of health care needs requests comprises: (a) the PBM inviting the health care suppliers to bid on fulfilling the health care needs requests; (b) the health care suppliers bidding on fulfilling the health care needs requests; and (c) the PBM selecting the winning bids, thereby selecting the health care suppliers to supply each of the end users health care needs requests. It is to be understood, however, that the present system does not require competitive bidding between pharmacies as a way of selecting the pharmacies to fill the prescriptions. Other decision processes may instead be used by the PBM to select the pharmacies (including current or previous relationships between the PBM and the pharmacies).

The present system may be used to fill new prescriptions and to fill refill prescriptions. When refilling prescriptions, the patient may either contact the pharmacy or the PBM to renew the prescription. Both alternatives are contemplated within the scope of the present invention.

In further aspects, the present invention also presents an on-screen clinical interface to the patient (when the patient is sending their prescription request to the PBM). The clinical interface preferably provides prescription information, and additional relevant information, including drug history, clinical values (lab results), family history, or other relevant information, and consent forms to the patient. The patient can accept or decline the information presented in the clinical interface. Additionally, a lab can submit clinical values on behalf of the patient with the patients authorization.

In various aspects, the patients may send their prescriptions to the PBM over the Internet, or through a call center. The choice of using the Internet or a call center may depend upon the particular prescription being filled. For example, specialized call centers may be used or required for specific disease or conditions.

In further optional aspects, the system allows the PBM to collect data on the pharmacies filling the prescriptions. This data can then be transmitted to the pharmacies as a cost for using the present inventive service. Such data may comprise outcome data based on patient and physician satisfaction surveys and/or information from regulatory agencies (state regulatory agencies, CMS, Office of Inspector General, etc).

Preferably, the PBM charges the pharmacies for using the present service, however, it is also optionally possible to charge the patients for using the service. This may be possible when the patients are given data about the pharmacy selected by the PBM to fill their prescription. Such data given to the patients may include data about prescription fulfillment and order tracking.

The pharmacies that are selected for prescription fulfillment may be selected by the PBM itself, or may be selected by clients of the PBM. Such clients may be HMOs, PPOs and other health management organizations. Optionally, the participating patients may simply be employees of the clients of the PBM (i.e. patients covered by health management organizations that contract with the PBM).

It is to be understood that the present invention is not limited to fulfilling prescriptions. For example, in other aspects the health care needs requests are requests for durable medical equipment, and the health care suppliers are durable medical equipment suppliers. As such, any reference herein to "patients" applies equally to "end users" in general. Also, any reference herein to "pharmacies" applies equally to "durable medical equipment suppliers".

The present invention also provides an Internet-based health care needs fulfillment system, comprising: (a) a sub-system for a PBM to contract with a plurality of health care suppliers to fulfill a plurality of health care needs requests; (b) a sub-system for receiving individual health care needs requests from end users; and (c) a sub-system for alerting selected health care suppliers to fulfill the end users' individual health care needs requests, after the PBM has selected the health care suppliers to supply each of the end users' individual health care needs requests.

Sub-systems may also be included for the patients to request re-filling of the prescriptions, and for presenting an on-screen clinical interface to the patient. The sub-system for receiving the prescriptions from the patients may be Internet-based, or it may be a call center, or some combination of these. A sub-system for collecting data on the pharmacies filling of the prescriptions, and/or the patients use of the prescriptions, may also be included.

In summary, a benefit of the present invention to the patients is that they are quickly and efficiently provided with prescription fulfillment. Should the patient have any questions or concerns, these can be directed to the PBM for answers or assistance.

A benefit to the PBM is that its clients are pleased with the convenience and efficiency of the system (since the PBM is able to use its own unique expertise to select the best pharmacy to fill any particular prescription, or prescriptions).

Lastly, a benefit to the pharmacies is that they contract in large "bulk orders" of prescriptions. Most large pharmacies (be they mail order or retail) do not have time to or want to process "requests for bids" on individual prescriptions. Instead, since their volume of fulfillment work is high, they would prefer to contract directly with a PBM. Preferably, these pharmacies simply provide the PBM with their capabilities list, and then let the PBM refer the prescriptions out directly for fulfillment without prolonged bidding step procedures for each prescription. The pharmacies also benefit from increased and continued business that comes with having satisfied customers. By securing a contract to supply a buck purchase of medication, the pharmacy is able to secure a large amount of business, thereby enabling it to increase its inventories of particular medications, as required by the PBM.

DETAILED DESCRIPTION OF THE DRAWINGS

Figure 1:
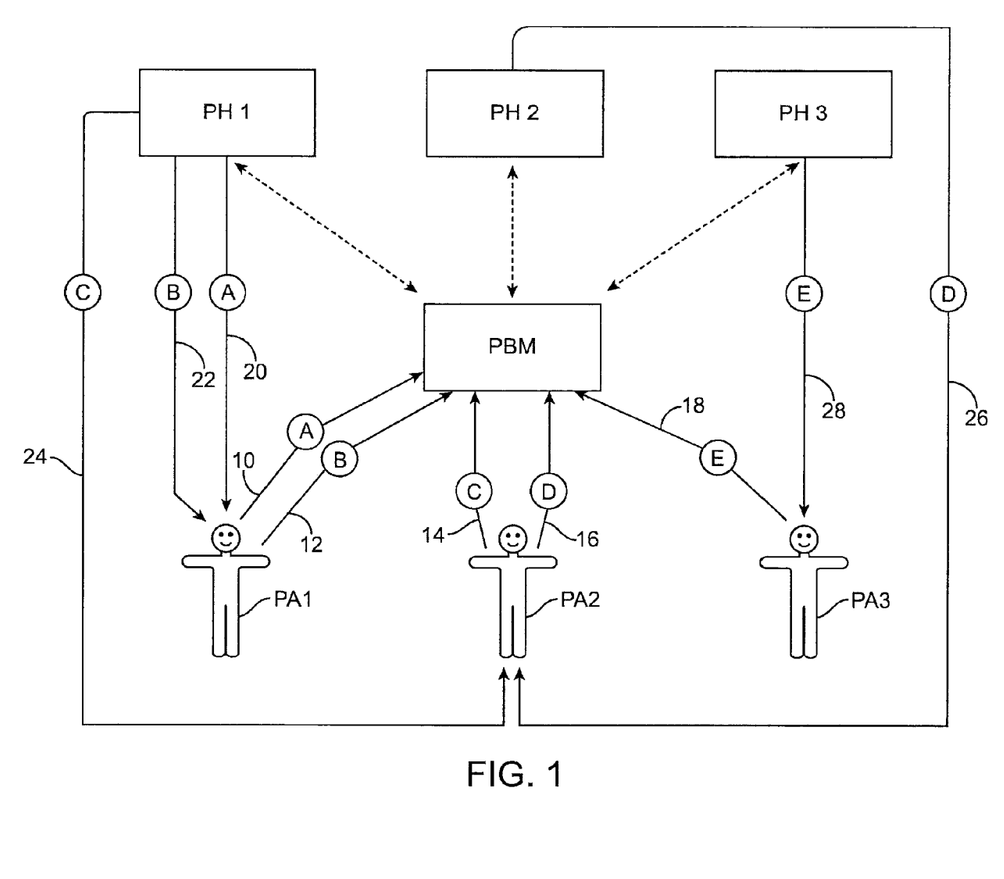
FIG. 1 is a simplified overview of the parties to the present invention, showing an example of prescription medication fulfillment.

FIG. 1 illustrates the parties to the present invention, as follows. A single PBM co-ordinates and operates a system for prescription fulfillment in which a three different patients PA1, PA2 and PA3 submit their prescriptions for fulfillment. (Note: only three patients are illustrated here for clarity. In practice, thousands of patients may simultaneously use the present system). In this example, three pharmacies PH1, PH2 and PH3 are selected to fill each of the prescriptions for patients PA1, PA2 and PA3. (Note: only three pharmacies are illustrated here for clarity. In practice, many pharmacies (including both retail and mail order) may simultaneously use the present system—as determined by the PBM). As will be fully explained herein, it is the PBM who selects which pharmacy will fulfill each of the different patients' prescriptions. Thus, different pharmacies may fulfill different prescriptions and for different patients (and at different times). All combinations are possible, and FIG. 1 merely shows one example of system operation.

In this example, patient PA1 has to fill two prescription requests 10 (for medication "A") and 12 (for medication "B"). Patient PA1 simply sends prescription requests 10 and 12 to the PBM, preferably by using an on-line interface and/or through an optional call center. Similarly, patient PA2 sends prescription requests 14 (for medication "C") and 16 (for medication "D") to the PBM. Patient PA3 has only one prescription request 18 (for medication "E"). Note: The various combinations of prescription requests 10, 12, 14, 16 and 18 may be submitted simultaneously to the PBM, or in any order.

All of these prescription requests 10, 12, 14, 16 and 18 are received by the PBM. In accordance with the present invention, the PBM selects which pharmacies PH1, PH2 and PH3 will fulfill the prescription needs of patients PA1, PA2 and PA3. For example, PH1 is selected by the PBM as the preferred supplier of medications A, B and C; and pharmacy PH2 is selected by the PBM as the preferred supplier of medication D, and pharmacy PH3 is selected by the PBM as the preferred supplier of medication E. As such, medication A is supplied at step 20, medication B is supplied at step 22, medication C is supplied at step 24, medication D is supplied at step 26, and medication E is supplied at step 28. As can be seen in the example of FIG. 1, patient PA1 receives all of his/her medication from pharmacy PH1, patient PA1 receives his/her medication from both pharmacies PH1 and PH2, and patient PA3 receives all of his/her medication from pharmacy PH3. It is to be understood that FIG. 1 is merely one example of the interaction between the parties to the present invention. In practice, the medications supplied by each of the pharmacies to each of the patients may change at different times, and in different situations. Also, additional pharmacies (not shown) may participate in the system but not be selected by the PBM to fulfill any prescription requests.

For clarity, simplified communications between the PBM and each of pharmacies PH1, PH2 and PH3 are shown in dotted lines. As will be explained, this communication is two way, with the individual pharmacies PH1, PH2 and PH3 contracting with the PBM to supply various medications, and the PBM alerting each of the pharmacies as to which patient prescriptions are to be filled by them.

In the example of FIG. 1, the PBM receives prescription requests from patients PA1, PA2 and PA3 for fulfillment by pharmacies PH1, PH2 and PH3. It is to be understood, however, that the present invention is not limited to pharmacies fulfilling prescriptions. In alternate aspects, it can be used for durable medical equipment suppliers to supply durable medical equipment. Durable medical equipment suppliers may include medical beds, walkers, physical therapy equipment, oxygen tanks, etc. This makes the present invention applicable to hospice and hospital services, not just pharmacies. As such, the present invention is more broadly defined as fulfilling the "health care needs requests" of end users (who may or may not be patients with "prescription requests").

As such, the present invention more broadly provides a method of operating a health care needs fulfillment system, comprising: (a) the PBM contracting with a plurality of health care suppliers to fulfill a plurality of health care needs requests; (b) end users sending individual health care needs requests to the PBM; (c) the PBM selecting the health care suppliers to supply each of the end users' individual health care needs requests; and (d) the PBM alerting the selected health care suppliers to fulfill the end users' individual health care needs requests.

Using the illustration of FIG. 1, the present invention provides a method of operating a virtual pharmacy, by: (a) the PBM contracting with pharmacies PH1, PH2 and PH3 to fulfill prescription requests; (b) patients PA1, PA2 and PA3 sending their prescription requests to the PBM; (c) the PBM selecting the particular pharmacy or pharmacies PH1, PH2 and PH3 to fulfill each of the prescription requests; and (d) the PBM alerting pharmacies PH1, PH2 and PH3 to fulfill the particular patients' prescription requests.

In one aspect of the invention, the PBM uses its unique decision making skills to select the particular pharmacy PH1, PH2 and/or PH3 to fulfill each of medications A, B, C, D and E. This selection may be made on the basis of price, the basis of the locations of the pharmacy and the patient, or even on the basis of pharmacy expertise. Therefore, the various medications supplied to the patients at steps 20, 22, 24, 26, and 28 may be filled by mail-order or in person.

In an alternate approach, the PBM contracting with pharmacies PH1, PH2 and PH3 to fulfill prescription requests comprises: (a) the PBM inviting pharmacies PH1, PH2 and PH3 to bid on fulfilling prescriptions; (b) pharmacies PH1, PH2 and PH3 bidding on fulfilling the prescriptions requests; and (c) the PBM selecting winning bids, thereby selecting the appropriate pharmacy PH1, PH2 and/or PH3 to supply each of the prescriptions.

In various aspects, the prescriptions fulfilled at steps 20, 22, 24, 26 and 28 may be new prescriptions, or they may be refill prescriptions. In some optional aspects of the invention, patients PA1, PA2 and PA3 may directly contact the previously selected pharmacy to renew the prescription. For example, patient PA1 may directly contact pharmacy PH1 to renew his/her prescription for medications A or B. Similarly, patient PA2 may directly contact pharmacy PH1 to renew his/her prescription for medications C, and directly contact pharmacy PH2 to renew his/her prescription for medication D.

Figure 2:
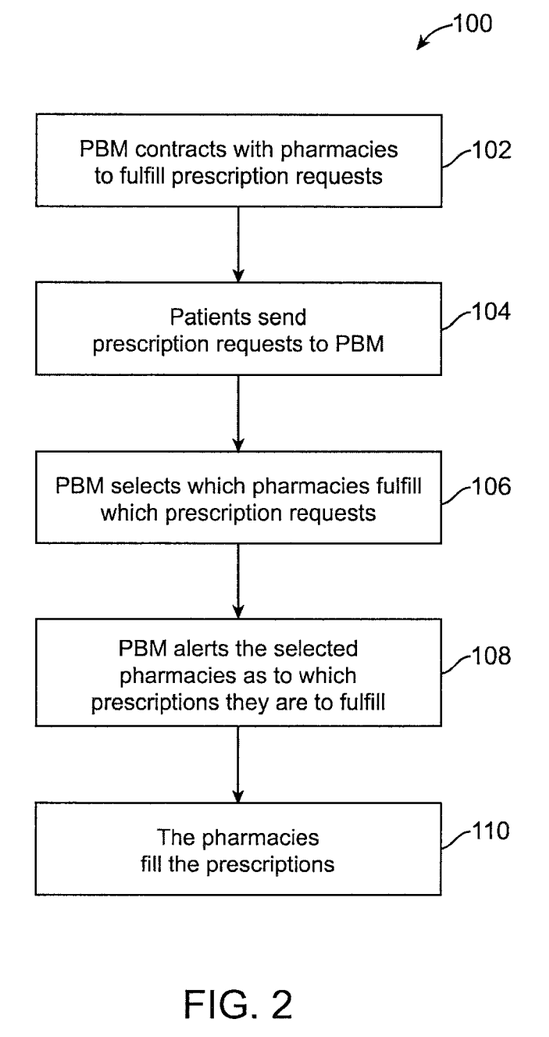
FIG. 2 is a flow chart of the method steps of a preferred aspect of the present invention.

Turning now to FIG. 2, a flow chart of the method steps of a preferred aspect of the present invention will be set forth, as follows.

The present invention provides a method 100 of operating a health care needs fulfillment system, comprising: (a) step 102 in which the PBM contracts with a plurality of pharmacies (PH1, PH2 and PH3 in FIG. 1) to fulfill a plurality of prescription requests (10, 12, 14, 16 and 18 in FIG. 1); (b) step 104 in which patients (PA1, PA2 and PA3) send their individual prescription requests to the PBM; (c) step 106 in which the PBM selects the pharmacies to fulfill each of the patients' individual prescription requests; and (d) step 108 in which the PBM alerts the selected pharmacies to fulfill the patients' individual prescription requests. Lastly, at step 110 the selected pharmacies fulfill the individual patients' individual prescription requests (i.e.: in FIG. 1 pharmacy PH1 sends medication A and B to patient PA1, and sends medication C to patient PA2). Step 110, may be carried out by mail-order or in person (depending upon the pharmacy selected by the PBM).

Step 102 may be carried out by the PBM selecting the most appropriate pharmacy to fill the prescriptions on the basis of price, the basis of the relative locations of the pharmacy and the patient, the basis of pharmacy expertise, and/or any other criteria important to the pharmacy. The PBM may rate the pharmacies as to service, pricing, auditing, reporting, fulfillment, types of pharmaceuticals handled, etc. Advantageously, the PBM could change the selection of the pharmacy to fill the prescription if the prescription is to be re-filled and the pricing conditions change. The patient thus is pleased, by having the burden lifted of choosing a pharmacy, along with checking to be sure his/her plan is accepted by that pharmacy, and receiving prescriptions in the mail in a timely manner with quality service. The payor also is pleased, since the plan members are content and plan costs are economically reasonable.

Having the PBM select the best pharmacy is particularly important in the case of biotherapeutic drugs, which are usually very expensive and targeted specifically at a very limited condition. The PBM would desire to have control over the dispensing of such drugs, especially so that the drugs (and costs) are not wasted on conditions for which regular drugs are adequate. Moreover, biotherapeutic drugs are mainly available only from "specialty pharmacies" and usually are prescribed within hospitals and hospices so that they can be properly administered. Also in most cases the patient must be present when the drug is initially dispensed or administered so they know how to use it. Also, biotherapeutics and similar special pharmaceuticals typically cannot be dispensed by regular mail order, and normally require special "cold pack" packaging and must be delivered within no more than one day.

An important optional (but preferred) element in the present invention is a function of the PBM continually reviewing the performance of the selected pharmacies in cost control, and particularly in the area of cost reduction by increasing the proportion of lower cost generic drugs in the overall mixed of dispensed drugs. In the past mail order pharmacies and some mandate plans have accomplished this simply by requiring substitution of generics unless a physician has required otherwise.

In addition, contracts between the PBM and each of the pharmacies PH1, PH2 and PH3 can include provisions that encourage pharmacists to communicate with their consumers about the value of generic drugs, which is especially effective in the retail pharmacy setting where the pharmacist and the consumer meet directly. The PBM also can communicate the same message through its regular communications with payers and their employees and members.

In optional embodiments, the present invention also includes the PBM continually reviewing the performance of the selected pharmacies, and also periodic adjustment of the discount and cost structures to reward those pharmacies who are operating at greater-than-expected performance. Conversely, incentives can be provided to under-performing pharmacies to improve.

Figure 3:
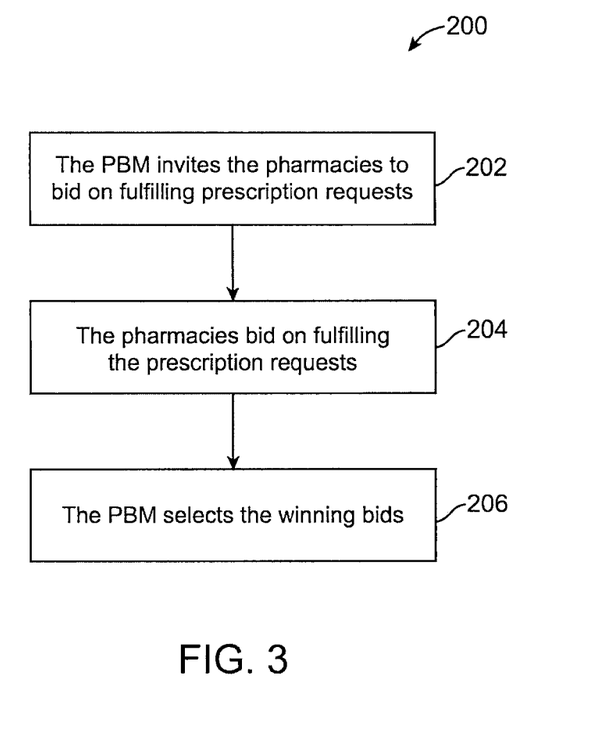
FIG. 3 is a flow chart of additional optional method steps taken when the PBM invites a number of pharmacies to bid on fulfilling prescriptions.

Step 102 is preferably carried out through an on line computer interface. An optional bidding system is shown in FIG. 3 (see below) for the selection of pharmacies.

Step 104 is preferably carried out through an on line computer interface as well. Optionally, however, step 104 may also be carried out through a call center. In alternate embodiments, a layered structure may be used in the call centers so that difficult or complex issues can be handled by, or referred to, at higher levels in the call centers. The call centers may optionally be staffed by doctors and pharmacists. The PBM may itself may have an in-house call center.

At step 104, the patient may send new or refill prescription requests to the PBM. In the case of new prescriptions, method 100 is carried out as set forth in FIG. 2. However, in the case of refill prescriptions, the alternative method of the patients directly contacting the (previously selected) pharmacy to obtain the prescription refill is also contemplated within the scope of the present invention.

An additional benefit of the present invention is its ability to simplify prescription ordering procedures for the pharmacies. Under many current prior art plans, the determination of the proper reporting identification for the prescription in terms of medication, dosage and quantity is the function of the individual pharmacy at the outset of seeking plan approval and reimbursement for filling of a prescription. If the pharmacist incorrectly designates a prescription when entering it into a plan reimbursement system, it will often end up being routed to the incorrect PBM or PBM vendor responsible for approving and/or supplying the medication. In such cases, the prescription filling is disapproved since it was improperly identified by the pharmacist, and the entire process must be restarted. This is troublesome and time-consuming for the pharmacist and annoying to the consumer, who must wait an added period of time for correct filling of his/her prescription. Under the present plan invention, however, the PBM provides approval and authorization for filing of the prescription. As the PBM has pre-approved the fulfillment of the prescription and itself provides the order, errors in routing are virtually eliminated and prescription fulfillment is expedited, to the benefit of both the pharmacist and the consumer.

Furthermore, the present invention provides a system and method for a consumer to provide his/her prescription to a PBM directly and to deal directly with the same PBM even if the prescription-filing pharmacy may change. Additionally, the pharmacy is no longer required to obtain a determination of eligibility and the reimbursement rate before filling each individual prescription because the price was determined by the bidding process and each prescription is preferably pre-approved before it is sent by the PBM to the pharmacy. As such, the pharmacist no longer has to determine under which specific plan the prescription request is to be adjudicated or whether two or more PBMs or payors may be involved.

Because the patient interfaces with the PBM instead of the selected pharmacy, any questions or other communication regarding the prescription is between the patient and the PBM. This means that the PBM is free to re-select a different pharmacy to re-fill a patient's prescription without concerns about interrupting the relationship between the patient and the selected pharmacy. In addition, allowing the refills to be routed through the PBM has the advantage of keeping in close contact with the patients. This permits the PBM to use the refill information from each patient to track how the pharmacy has performed for patient with prior service as to the prescription being refilled (e.g., such as for service, labeling, speed of fulfillment).

Cost-savings also stem from the patient interfacing directly with the PBM such that the PBM can discuss the option of using lower-priced generic drug equivalents with the patient. Generic drugs represent the major share of the prescription market, generally being about 75% of reimbursements nationally. There are numerous generic medication providers, which fosters competition between them, while most of the brand name (proprietary) drugs are available only from a single producer. If agreed by the patient, the PBM can thereby instruct the selected pharmacy to supply a generic equivalent drug.

In another alternative embodiment, the PBM is granted permission by the patient to contact the prescribing physician with any questions about the prescription. For example, if the PBM has reviewed the prescription and determines a generic equivalent may be an acceptable substitute, the PBM can contact the prescribing physician about a potential change to a generic equivalent thus saving money, and not requiring the consumer to spend time contacting the physician about the use of the generic equivalent.

Another cost and time saving advantage of the present plan system is that PBM coverage of the prescription is pre-approved before the prescription is filled by the selected pharmacy. At the time the prescription is ordered from the selected pharmacy, the PBM provides pre-approval to the selected pharmacy, along with the proper coding for billing. As such, the selected pharmacy does not have to invest the time in seeking pre-approval and is assured that the coding for its billing to the PBM is correct.

A further aspect of step 104 is that, when carried out on line, an on-screen clinical interface may optionally be presented to the patients. This clinical interface may provide prescription information to the patients, and may require the patients to consent to receiving the information presented on the on-screen clinical interface. Current law requires a pharmacy, when it opens a new prescription or changes a previous prescription, to offer a "clinical interface" with the patient, to discuss what the drug is, what the dosage is, how often to take it, what it's for, etc. An example is for blood pressure medicine, where the pharmacist will make sure that the patient understands that while high blood pressure is asymptomatic, the patient must be sure to take the medication regularly, even though they feel well. A patient does not have to accept the offer of an interface. Thus, the patient could decide to accept or decline the clinical interface.

In another example, the prescribing physician may prescribe a specialty pharmaceutic such as a biotherapeutic drug. Those of skill in the art are capable of determining what drugs are considered biotherapeutic drugs. Because these drugs are very expensive and must be carefully dispensed, the PBM may contact the physician about potential equivalent and lower-cost medications or about special dispensing instructions. Indeed, because the PBM may have contact with the prescribing physician, any questions about the prescription could be efficiently answered and any problems quickly resolved.

At step 106, the PBM selects which pharmacies fulfill each patients' prescription requests. Step 106 may be carried out by the PBM in a manner similar to step 102. Specifically, the PBM may select the most appropriate pharmacy to fill each patient's prescription on the basis of price, locations of the pharmacy and the patient, pharmacy expertise, and/or any other criteria important to the pharmacy.

In further optional aspects, the PBM may also collect data on the pharmacies filling the prescriptions, and/or the patients' use of these prescriptions. This data may comprise outcome data based on patient and physician satisfaction surveys and/or information from regulatory agencies (state regulatory agencies, CMS, Office of Inspector General, etc). The PBM may then send the collected data to the pharmacies, and charge them for this service. And/or, the PBM may then send the collected data to the patients, and charge them for this service. In addition, patient specific data may be compiled and saved for the patient himself/herself. This would give the patient a specific location in which to locate their prescription order tracking and personal medical history information. In addition, the PBM can use the present system as a database to include identification of each subscribing pharmacy and its physical location (for local retail pharmacies) or mailing address (for mail-order pharmacies), a list of the medications which the pharmacy carries in stock or can readily obtain, and the pharmacy's current retail price for the various standard dosages and forms (liquid, tablet, etc.) of each medication.

As was stated above, the PBM selects the pharmacies at step 106. Optionally however, the pharmacies may also be selected by clients of the PBM. For example, such clients may include managed care organizations such as HMOs and PPOs. As such, the patients that participate in the present system may be clients (or employees) of the clients of the PBM. Selection of the pharmacies may be done by the PBM and the clients of the PBM working together.

Step 108 is preferably carried out in an on line interface between the PBM and the pharmacies PH1, PH2 and PH3. Alternatively, the PBM may contact the pharmacies by phone, fax or e-mail to alert them as to which specific prescriptions they have been selected to fill for which specific patients. At this stage, the PBM may also send any specific fulfillment instructions to the pharmacy that would be required in the case of non-standard or special order medications.

FIG. 3 sets forth a flow chart of the method steps of an optional bidding system used by the PBM to select (and then contract with) preferred pharmacies, as follows.

The present invention provides a bidding method 200 of the PBM contracting with a plurality of pharmacies (PH1, PH2 and PH3 in FIG. 1) to fulfill a plurality of pharmacy requests (10, 12, 14, 16 and 18 in FIG. 1) comprising: (a) step 202 in which the PBM invites the pharmacies to bid on fulfilling prescription requests; (b) step 204 in which the pharmacies bid on fulfilling the pharmacy requests; and (c) step 206 in which the PBM selects the winning bids, thereby selecting the pharmacy to supply each of the prescription requests.

It should be understood that the PBM will not typically solicit bids from pharmacies each time a new prescription is received from a customer. Indeed, for many commonly-prescribed medications, the PBM will prefer to solicit bids on a periodical basis (i.e. quarterly) from pharmacies in various geographic areas and will select one of those pharmacies to provide that certain medication to all of its customer's with prescriptions for that medication over that time period. For example, a PBM could quarterly solicit bids for a certain blood pressure medication, receive the bids, consider price and the other variables and choose a selected pharmacy to fill all consumer's prescriptions for that popular drug over the next yearly quarter. After that time period has expired, the PBM could re-solicit bids and choose the same selected pharmacy or another selected pharmacy. Because the patient interfaces with the PBM all questions about the medication or filling of the prescription are directed to the PBM, thus the fact that the selected pharmacy may change periodically should not concern the patient. For more unusual prescriptions or medical devices, however, the PBM may prefer to solicit bids on a per-prescription basis.

The PBM may prefer to send out a single bid for a single medication or a single type of prescription; however, the PBM may equally decide to send out a single bid for a group of (related or non-related) medications together. In various options, the bidding may be based on the PBM presenting a price ranges and/or particular guidelines to the pharmacies. Such ranges may set form payment conditions for the PBM to the pharmacies or ancillary services (member-specific counseling, delivery services, etc).

The decision as to what contract or supply contract is bid upon rests with the PBM. The present invention thereby encompasses any form of bidding and contracting developed or used by the PBM.

In preferred aspects, the present system is structured around an Internet site on which resides software embodying the present system and method. As such, the present invention may provide an Internet-based health care needs fulfillment system, comprising: (a) a sub-system for a PBM to contract with a plurality of health care suppliers to fulfill a plurality of health care needs requests; (b) a sub-system for receiving individual health care needs requests from end users; and (c) a sub-system for alerting selected health care suppliers to fulfill the end users' individual health care needs requests, after the PBM has selected the health care suppliers to supply each of the end users' individual health care needs requests.

Further sub-systems may be provided for: (a) patients to request re-filling of the prescriptions, (b) presenting an on-screen clinical interface to the patient, (c) collecting data on the pharmacies filling the prescriptions, or the patients submitting prescription requests. In optional aspects where the PBM uses bidding to contract with selected pharmacies, further sub-systems may be included to: (a) invite the health care suppliers to bid on fulfilling the health care needs requests; and (b) receive bids from the health care suppliers.

In operation, different aspects of the on line Internet side embodying the present invention may be viewable to different parties. For example, the entire system is controlled (and viewable by) the PBM. However, the patients need only see the interface at step 104 through which they submit their prescription requests to the PBM.

As can be appreciated, the present invention broadly provides a "virtual pharmacy" that operates for a PBM to obtain the best value for products and services received by patients (or other end users).

Although several embodiments of the invention have has been described above by way of example only, it will be understood by those skilled in the field that numerous variations and modifications may be made to the disclosed embodiments without departing from the scope or spirit of the invention, as it is defined by the appended claims.

What is claimed is:

1. An Internet-based health care needs fulfillment system, comprising:
a computing sub-system for a prescription benefit manager to solicit a plurality of pharmacies to participate in a bidding process;
a computing sub-system for the prescription benefit manager to receive a plurality of bid submissions from the plurality of pharmacies, wherein each bid submission comprises a bid to fulfill a bulk quantity of future prescriptions for a drug, each bid comprising pricing information for fulfilling the future prescriptions for the drug;
a computing sub-system for receiving at least one prescription from a patient;
a computing sub-system for the prescription benefit manager to select a first pharmacy from the plurality of pharmacies that submitted a bid to fulfill the at least one prescription, wherein the first pharmacy is selected by the prescription benefit manager and not the patient based on a comparison of the plurality of pharmacies to one another, wherein the comparison is based at least in part on the bid submissions and at least one of: a fulfillment price for the at least one prescription of each of the plurality of pharmacies, a location of each of the plurality of pharmacies, and an expertise level with regard to the at least one prescription of each of the plurality of pharmacies; a sub-system for contacting the selected first pharmacy to send the at least one prescription to the selected first pharmacy for fulfillment; and
a computing sub-system for collecting data on the selected first pharmacy fulfilling the at least one prescription.

2. The system of claim 1, wherein the sub-system for receiving the at least one prescription from the patient is an Internet-based sub-system.

3. The system of claim 1, wherein the comparison is based on the fulfillment price for the at least one request for the prescription of each of the plurality of pharmacies.

4. The system of claim 1, wherein the comparison is based on the location of each of the plurality of pharmacies.

5. The system of claim 1, wherein the comparison is based on the expertise level with regard to the at least one request for the prescription of each of the plurality of pharmacies.

6. An Internet-based health care needs fulfillment system, comprising:
a computing sub-system for a first user to solicit a plurality of health care product suppliers to participate in a bidding process;
a computing sub-system for the first user to receive a plurality of bid submissions from the plurality of health care product suppliers, wherein each bid submission comprises a bid to fulfill a bulk quantity of future health care product requests for a particular health care product, each bid comprising pricing information for fulfilling the future health care product requests for the particular health care product;
a computing sub-system for receiving at least one health care product request from a second user;

a computing sub-system for the first user to select a first health care product supplier from the plurality of health care product suppliers that submitted a bid to fulfill the at least one health care product request, wherein the first health care product supplier is selected by the first user and not the second user based on a comparison of the plurality of health care product suppliers to one another, wherein the comparison is based at least in part on the bid submissions and at least one of: a fulfillment price for the at least one health care product request of each of the plurality of health care product suppliers, a location of each of the plurality of health care product suppliers, and an expertise level with regard to the at least one health care product request of each of the plurality of health care product suppliers;

a computing sub-system for contacting the selected first health care product supplier to send the at least one health care product request to the first health care product supplier for fulfillment; and a computing sub-system for collecting data on the selected first health care product supplier fulfilling the at least one health care product request.

7. The system of claim 6, wherein the second user is a patient.

8. The system of claim 7, further comprising:
a sub-system for the patient to request re-filling of the at least one health care product request.

9. The system of claim 8, wherein the sub-system for the patient to request re-filling of the at least one health care product request comprises a system for the patient to request re-filling of the at least one health care product request from the first user.

10. The system of claim 7, further comprising:
a sub-system for presenting an on-screen interface to the patient.

11. The system of claim 6, wherein the sub-system for receiving the at least one health care product request from the second user is Internet based.

12. The system of claim 6, wherein the comparison is based on the expertise level with regard to the at least one health care product request of each of the plurality of health care product suppliers.

13. The system of claim 6, wherein the first user is a prescription benefit manager (PBM) that manages a health plan for the second user.

14. The system of claim 6, wherein the sub-system for contacting the selected first health care product supplier contacts the selected first health care product supplier via e-mail.

15. The system of claim 6, wherein the plurality of health care product suppliers comprise durable medical equipment suppliers, and wherein the at least one health care product request comprises a request for durable medical equipment.

16. The system of claim 6, wherein the plurality of health care product suppliers comprise pharmacies, and wherein the at least one health care product request comprises a prescription.

17. The system of claim 6, wherein the first user has pre-approved fulfillment of the at least one health care product request of the second user prior to sending the request to the selected first health care product supplier.

18. The system of claim 6, wherein the sub-system controlled by the first user for selecting the first health care product supplier from the plurality of health care product suppliers to fulfill the at least one health care product request selects the first health care product supplier to fulfill requests for health care product of a type requested in the at least one health care product request prior to receiving the at least one health care product request from the second user.

19. An Internet-based health care needs fulfillment system, comprising:
a computing sub-system for a first user to select a plurality of health care product suppliers to fulfill received health care product requests;

a computing sub-system controlled by the first user to receive one or more bids from the plurality of health care product suppliers, wherein each bid comprises a price at which to fulfill future requests received by the first user for a health care product of a first type;

a computing sub-system for selecting a first bid from the one or more bids based at least in part on each price;

a computing sub-system for receiving at least one health care product request of the first type from a second user;

a computing sub-system for the first user to select a first health care product supplier from the plurality of health care product suppliers to fulfill the at least one health care product request, wherein the first health care product supplier is the health care product supplier associated with the first bid;

a computing sub-system for contacting the selected first health care product supplier to fulfill the at least one health care product request; and a computing sub-system for collecting data on the selected first health care product supplier fulfilling the at least one health care product request.

* * * * *